United States Patent [19]

Gunkel et al.

[11] 4,280,905
[45] Jul. 28, 1981

[54] CHROMATOGRAPHY COLUMN

[75] Inventors: Werner Gunkel, Rossdorf; Friedhelm Eisenbeiss, Griesheim, both of Fed. Rep. of Germany

[73] Assignee: Merck Patent Gesellschaft mit beschränkter Haftung, Darmstadt, Fed. Rep. of Germany

[21] Appl. No.: 173,307

[22] Filed: Jul. 29, 1980

[30] Foreign Application Priority Data

Jul. 31, 1979 [DE] Fed. Rep. of Germany ....... 2930962

[51] Int. Cl.³ .............................................. B01D 15/08
[52] U.S. Cl. ................................... 210/198.2; 210/351
[58] Field of Search ..................... 210/198.2, 351, 356; 55/386

[56] References Cited

U.S. PATENT DOCUMENTS

| 3,855,130 | 12/1974 | Randau | 210/198.2 |
| 4,187,177 | 2/1980 | Stahl | 210/198.2 |

FOREIGN PATENT DOCUMENTS

| 1955276 | 6/1972 | Fed. Rep. of Germany | 210/198.2 |
| 2739860 | 3/1979 | Fed. Rep. of Germany | 210/198.2 |

Primary Examiner—John Adee
Attorney, Agent, or Firm—Millen & White

[57] ABSTRACT

A chromatography column adapted for high pressure chromatography is characterized by a tubular membrane separating a glass tube from the pressurized area between the glass tube and a pressure tube adapted to receive a pressurizing fluid. Changing of the glass tube is facilitated by annular seals at each end of the glass tube against which an adjustable threaded plug, fitted in one of a pair of screw caps fitted on each end of the pressure tube, exerts sealing pressure.

8 Claims, 1 Drawing Figure

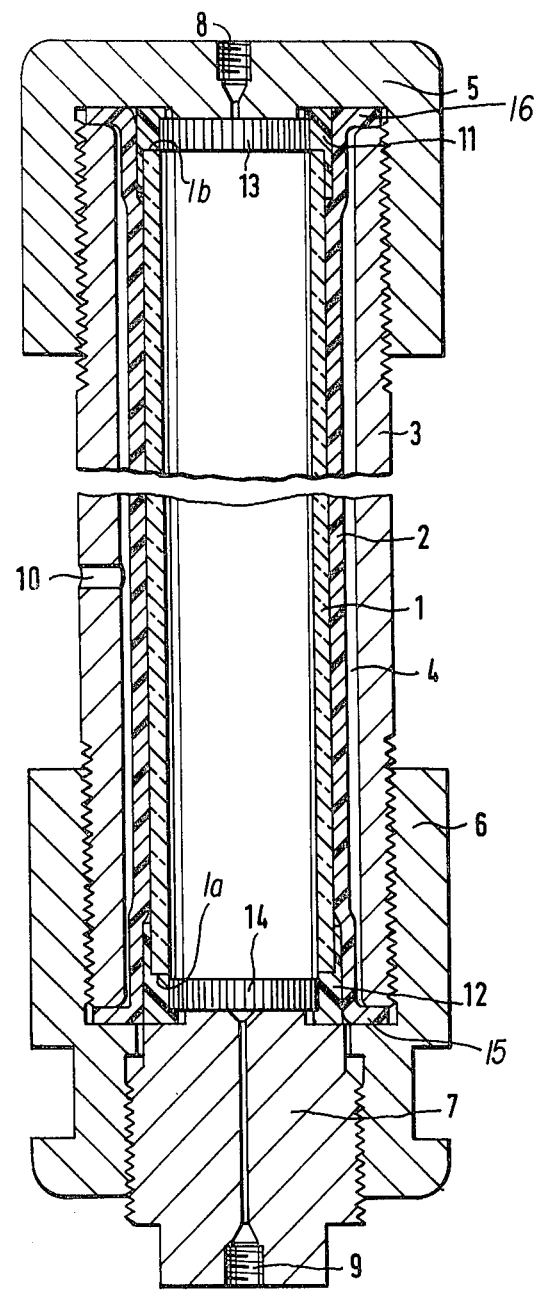

CHROMATOGRAPHY COLUMN

BACKGROUND OF THE INVENTION

This invention relates to a column adapted for high pressure liquid chromatography of the type having a glass column adapted to be filled with the sorbent and which is surrounded concentrically, with an intermediate space being maintained therebetween, by a pressure tube.

Such columns are known, for example, from German Utility Model No. 7,146,039, German Offenlegungsschrift No. 2,329,286 and German Auslegeschrift No. 2,524,751. In these known columns, the intermediate space between the glass column and the pressure tube is filled with the eluent, as the pressure liquid, used for the chromatographic separation by connecting the intermediate space to the eluent feed, so that the pressure acting externally on the glass column is the same as or greater than that inside the column and the glass column thus cannot explode from the pressure of the eluent.

It has been proposed to seal off the intermediate space from the ends of the column so that the eluent contained in the intermediate space cannot mix with the eluent entering at the top of the column. In German Offenlegungsschrift No. 2,329,286, this is achieved by sealing off the ends of the column from the intermediate space with O-rings, which has the disadvantage that the glass column must be matched precisely to the length of the pressure tube, with minimum tolerance.

It is thus proposed in German Auslegeschrift No. 2,524,751 to seal off the glass column from the intermediate space with a seal of the stuffing box type, whereby even relatively large differences in length of the glass column can be tolerated. Polytetrafluoroethylene seals are used as the stuffing box-type seals. Although these seals are resistant towards the eluent present in the intermediate space, they have a relatively low elasticity, so that the diameter tolerances of the glass column to be compensated by the seals are small. These stuffing box-type circumferential seals also make it very difficult to change the glass column. More specifically, in order to change the column, the screws at both ends of the pressure tube must be undone and at least one of the two such seals, which have been pressed firmly onto the glass tube, must be removed so that the glass column can be pulled out of the pressure tube. A further disadvantage of this construction is that a free space must be provided between the end of the column and the screw connection of the pressure tube in order to compensate for length variations in the glass column. This means that the column is not firmly clamped in the longitudinal direction, so that leaks in the inflow and outflow capillaries, which necessarily fit in only relatively loosely, can very easily result.

It is an object of this invention to prove a column for high pressure liquid chromatography which uses simple head seals which permits easy change of the glass column and which permits the use of glass columns with relatively large variations both with respect to diameter and with respect to length, and in particular, which employs seals for the glass column which do not come into contact with the pressure fluid. Other objects will be apparent to those skilled in the art.

SUMMARY OF THE INVENTION

According to this invention, there is provided a chromatographic column adapted for high pressure liquid chromatography comprising a glass tube open at both ends and positioned axially within a pressure tube having an internal diameter larger than the external diameter of the glass tube so as to provide a circumferential intermediate space therebetween and having an aperature in the wall thereof to provide communication between the intermediate space and a source of a pressurizing fluid when the column is connected therewith; a pair of removable screw caps threadably mounted on respective ends of the pressure tube, each having an aperature therein communicating with respective ends of the glass tube and providing an inlet and outlet, respectively, for chromatography eluent; and sealing means for sealing the open ends of the glass column from the intermediate space, which column is characterized by the sealing means comprising a flexible tubular shaped membrane positioned in the intermediate space and extending the length of the glass tube so as to provide a sleeve therefor which separates the glass tube from the pressurizing fluid.

DESCRIPTION OF THE DRAWING

The drawing is an axial cross-sectional view of a preferred embodiment of the column of this invention.

As shown in the drawing, a glass column 1 is separated by a flexible membrane 2 from a pressure tube 3. An intermediate space 4 is provided between the pressure tube 3 and the flexible membrane. The ends of the pressure tube are threaded and fitted with a pair of screw caps 5 and 6 (union or cap nuts). The lower screw cap 6 has a threaded annular bore 6a into which a screw stopper 7 is fitted. The upper screw cap 5 and the screw stopper 7 are provided with outflow 8 and inflow 9 capillaries, respectively. It should be noted, however, that the direction of flow can be chosen freely, so that capillary 8 can be used as inflow and capillary 9 as outflow as well. Pressure tube 3 is provided with a connection fitting 10 for connecting the tube to a source of pressure fluid (not shown). The ends 1a and 1b of the glass tube 1 are sealed against the inner surface of upper screw cap 5 and the inner surface of screw stopper 7 by a pair of resilient annular seals 11 and 12. Fitted in annular seals 11 and 12 are a pair of glass frits 13 and 14 adapted to retain the chromatography medium (not shown) when the glass tube is filled therewith.

The flexible membrane 2 separates completely the glass column 1 from the pressure medium when it is introduced through connection fittings 10 so that no adverse effect can be manifested by the pressure medium against the seals 11 and 12.

The annular shoulder end portions 15 and 16 of flexible membrane 2 are clamped between the ends of the pressure tube 3 and screw caps 5 and 6. In order to facilitate easy replacement of the glass column 1, at least one of the union nuts is provided with a threaded bore 6a of a larger diameter than the external diameter of the glass tube 1, into which a screw stopper 7 is threaded.

In order to obtain a tighter seal, the ends 1a and 1b of the glass column 1 are preferably ground flat. The arrangement of the screw stopper 7 in the screw cap 6 also permits relatively large variations in length in the glass column 1, which variations are compensated for by the amount that screw stopper 7 is screwed into union cap 6.

In operation, membrane 2 is fitted into pressure tube 3 and the annular shoulders 15 and 16 of the end portions of membrane 2 are clamped to the respective ends of pressure tube 3 by screw caps 5 and 6.

The ends 1a and 1b of glass tube 1 are fitted with annular seals 11 and 12 and a glass frit 13 or 14 is positioned in one of the seals. The glass tube is filled with chromatography sorbent (not shown) and the other of glass frit 13 or 14 is then fitted into the other annular seal 11 or 12.

The filled glass tube 1 is then inserted into pressure tube 1 through the annular bore 6a in screw cap 6. Screw stopper 7 is then threaded into screw cap 6 until sealing pressure is exerted against annular seals 11 and 12.

Any fluid which can be forced through the connecting nozzle 10 can be used to compensate for or exceed the pressure existing inside the glass column 1 and thus prevent glass column 1 from exploding from the pressure of the chromatography eluent therein. The eluent used for the chromatographic separation can be used for this purpose by connecting a conventional T-joint connecting the source of the eluent to the feed capillary 9 and the connection fitting 10. However, a fluid different from that used for the chromatographic separation, such as air, water, oil or a similar medium, compressed to the required pressure, is preferably used. If air or water is used as the pressure fluid, the flexible membrane 2 can be made of virtually any type of elastic rubber. On the other hand, if the particular eluent used for the chromatography is employed at the pressure medium, the flexible membrane 2 is preferably made of a more inert material, such as polytetrafluoroethylene. Although this material has only a relatively low flexibility, it is nevertheless sufficient to provide the requisite seal between the ends of pressure tube 3 and screw caps 5 and 6.

To conduct a chromatographic separation in the column, the chromatography fluid is supplied to inlet aperture 9 and the pressure fluid is supplied to connection fitting 10 at a pressure which is at least the same as the internal pressure in the glass tube 1. The operating pressures employed depend largely on the strength of pressure tube 3 and can be up to several hundred bars.

Since only a single pressure tube 3, which can be formed of stainless steel or chrome plated brass, is required for each diameter of glass tube 1, the user can stock economically a large number of glass tubes 1 filled with the same or different chromatography media, for the most diverse chromatographic separation problems with relatively little financial expenditure, and can insert them into the pressure tube 3 when required in an extremely short time.

To change the glass tube 1 for another like tube, it is necessary only to remove screw stopper 7 and not screw caps 5 and 6, which hold the flexible membrane 2 is position. After removing glass tube 1 and inserting another filled glass tube, screw stopper 7 is merely screwed in again until the seals 11 and 12 between the glass tube 1 and cap 5 and screw stopper 7 are pressed into a sealing fit.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a chromatography column adapted for use in high pressure liquid chromatography comprising a glass tube open at both ends and positioned axially within a pressure tube having an internal diameter larger than the external diameter of the glass tube so as to provide a circumferential intermediate space therebetween and having an aperature in the wall thereof to provide communication between the intermediate space and a source of a pressurizing fluid when the column is connected therewith; a pair of removable screw caps threadably mounted on respective ends of the pressure tube, each having an aperature therein, communicating with respective ends of the glass tube and providing an inlet and outlet, respectively, for chromatography eluent; and sealing means for sealing the open ends of the glass column from the intermediate space, the improvement wherein the sealing means comprises a flexible tubular shaped membrane positioned in the intermediate space and extending the length of the glass tube so as to provide a sleeve therefor which separates the glass tube from the pressurizing fluid.

2. A column according to claim 1 wherein the flexible membrane is clamped at both ends thereof between respective ends of the pressure tube and the removable screw caps.

3. A column according to claim 2 wherein the clamped ends of the flexible membrane each comprises a ring-shaped annular flange extending transversely outwardly from the tubular shaped position of the membrane.

4. A column according to claim 1 wherein the sealing means comprises a pair of ring gaskets positioned between the ends of glass tube and the removable caps and wherein at least one of the removable caps comprises a threaded plug having a larger diameter than the glass tube and adapted to bring the gaskets in sealing relationship between the ends of the glass tube and the screw cap.

5. A column according to claim 4 wherein the ring gaskets are positioned within the respective ends of the tubular shaped membrane between the respective ends of the glass tube and the screw caps.

6. A column according to claim 5 wherein a pair of glass fritted discs are positioned in the ring gaskets, between the respective ends of the glass tube and the screw caps, and are adapted to retain chromatographic sorbent in the column when filled therewith.

7. A column according to claim 1 wherein the ends of the flexible membrane each comprise a ring-shaped annular flange extending transversely outwardly from the tubular shaped portion of the membrane, which is clamped between an end of the pressure tube and the screw cap threadably mounted thereon, wherein the ring-shaped annular flanges are clamped between respective ends of the pressure tube and the removable screw caps, wherein the sealing means comprises a pair of ring gaskets positioned between the ends of glass tube and the removable caps and wherein at least one of the removable caps comprises a threaded plug having a large diameter than the glass tube and adapted to bring the gaskets in sealing relationship between the ends of the glass tube and the screw caps and wherein the ring gaskets are positioned within the respective ends of the tubular shaped membrane between the respective ends of the glass tube and the screw caps.

8. A column according to claim 7 wherein a pair of glass fritted discs are positioned in the ring gaskets, between the respective ends of the glass tube and the screw caps, and are adapted to retain chromatographic sorbent in the column when filled therewith.

* * * * *